United States Patent

Ihn et al.

[11] Patent Number: 5,977,543
[45] Date of Patent: Nov. 2, 1999

[54] SAMPLE FOR TRANSMISSION ELECTRON MICROSCOPE ANALYSIS HAVING NO CONDUCTIVE MATERIAL IN THE ELECTRON BEAM PATH, AND ITS MANUFACTURING METHOD

[75] Inventors: Chan-kook Ihn; Chang-hyuk Ok, both of Suwon; Chang-sub Lim, Inchon, all of Rep. of Korea

[73] Assignee: Samsung Electronics Co., Ltd., Kyungki-do, Rep. of Korea

[21] Appl. No.: 08/908,982

[22] Filed: Aug. 8, 1997

[30] Foreign Application Priority Data

Sep. 19, 1996 [KR] Rep. of Korea ........................ 96-40945

[51] Int. Cl.6 ................................................... H01J 37/26
[52] U.S. Cl. ............................................................ 250/311
[58] Field of Search ................................. 250/311, 309, 250/307, 492.21

[56] References Cited

U.S. PATENT DOCUMENTS

| | | | |
|---|---|---|---|
| 5,124,645 | 6/1992 | Rhoden et al. | 250/311 |
| 5,225,683 | 7/1993 | Suzuki et al. | 250/311 |
| 5,440,123 | 8/1995 | Ikeda | 250/311 |
| 5,525,806 | 6/1996 | Iwasaki et al. | 250/311 |

*Primary Examiner*—Kiet T. Nguyen
*Attorney, Agent, or Firm*—Jones, Volentine, Steinberg & Whitt, L.L.P.

[57] ABSTRACT

A method for manufacturing a transmission electron microscope analysis sample of a substrate containing an insulating body or an insulating sample includes the steps of: depositing a conductive material on the sample and then polishing the sample using a focused ion beam. The polishing step removes the conductive material from the analysis point of the sample, such that an electron projection and transmission path is formed through the sample at the analysis point. However, the conductive material is not removed from the remainder of the sample, not including the analysis point, thereby forming a ground path for any charges formed in the sample.

18 Claims, 6 Drawing Sheets

SAMPLE FOR TRANSMISSION ELECTRON MICROSCOPE ANALYSIS HAVING NO CONDUCTIVE MATERIAL IN THE ELECTRON BEAM PATH, AND ITS MANUFACTURING METHOD

BACKGROUND OF THE INVENTION

1. Field of the Invention

The present invention relates to a sample for transmission electron microscope analysis, and a method for manufacturing the sample. The sample is formed as a thin piece, and is used to analyze a defect occurring in a predetermined portion of a semiconductor device using a transmission electron microscope ("TEM"). The sample and its manufacturing method are designed to prevent a possible electron charging during an ion-polishing step and during the TEM analysis, by forming a conductive material on the sample before the sample is subjected to focused ion beam (FIB) polishing.

2. Background of the Related Art

A transmission electron microscope is an instrument for analyzing the phase and the composition of a material, by projecting an incident electron beam accelerated with high potential on a thin sample (below about 1,000Å in thickness). TEM analysis is highly applicable to a sample of about 10 μm or less, and this thin sample can be manufactured only by a focused ion beam system (FIB).

A disadvantage of the TEM analysis of the prior art is that it is impracticable for use on a sample from a substrate that is an insulating material, or a semiconductor containing an insulating layer such as a liquid crystal display (LCD), because the sample becomes charged during the manufacturing procedures and during the TEM analysis.

The above-mentioned electron charging occurs during the TEM analysis as follows. Electrons projected on the sample permeate the sample, which results in back scattering and secondary electron emission. In all cases, the numerous incident charges lose their original energies and are captured in the sample. In the process, if the sample is conductive and has a ground path, the charges will flow away through them. If the sample, however, includes an insulating layer without any grounding path, there occurs a rapid charging even in a conductive sample so that the surface potential of the sample increases.

When the sample captures charges sufficient to raise its surface potential above a predetermined level, a phase to be analyzed cannot be obtained because the charges serve as electron mirrors which reflect the incident electron beam out of the sample. Further, the surface potential of the sample periodically varies due to the repeated emission and accumulation of secondary electrons.

Some have employed a method of depositing a conductive layer on the region to be analyzed in order to prevent the charging described above. But, this method is not applicable to TEM analysis, which analyzes an image obtained on a thin sample projected by an electron beam. This is because, when a TEM sample contains a conductive material, the actual image or phase of the sample overlaps with the image of the conductive material on the sample.

The TEM analysis is, therefore, practicable for a conductive sample with a ground path, but not applicable to the analysis of a sample containing an insulating layer or an insulating sample.

Despite these limitations on TEM analysis, it has become increasingly necessary in recent years to carry out TEM analysis for the microscopic region of semiconductor devices such as memory devices or the like, particularly an LCD whose base layer is made of glass ($SiO_2$).

In addition, the above-described charging effect on an insulating sample has a deleterious effect on the FIB grinding process in manufacturing the sample itself, by causing an over-etching or under-etching at the analysis point of the sample.

SUMMARY OF THE INVENTION

The present invention is directed to a sample for transmission electron microscope analysis, and a method for manufacturing the sample, that substantially overcomes one or more of the limitations and disadvantages of the related art.

An object of the present invention is to provide a transmission electron microscope analysis sample manufacturing method comprising the steps of depositing conductive material on a sample including the insulating body, or layer including insulating material, before a focused ion beam polishing process, thereby inducing the charge to a ground, and making TEM analysis possible.

Another object of the invention is to provide a TEM analysis sample manufacturing method capable of micro-polishing the sample by inducing the charge, formed in the sample containing the insulating layer and body, to the ground.

Still another object of the invention is to provide a TEM analysis sample manufacturing method capable of TEM analysis by inducing the charges, formed in the sample containing the insulating body and layer, to the ground.

To achieve these and other advantages and in accordance with the purpose of the present invention, as embodied and broadly described, a method of manufacturing a sample for transmission electron microscope analysis comprises the steps of: cutting a sample to a predetermined size, grinding the sample using a polishing process, and adhering the sample to a grid; and grinding the analysis point of the sample so thin that charges sufficiently permeate it with a focused ion beam, the step of grinding being carried out after the step of forming a conductive material on the surface of the sample.

The analysis sample can be manufactured from an insulating body or layer including insulating materials. For example, such a sample is used for forming a liquid crystal display. The conductive material is preferably formed on both the sample and a grid to which the sample is adhered. The conductive material, such as gold or platinum, can be deposited to a thickness of over 50 Å by a coating and sputtering deposition method.

In the sample for transmission electron microscope analysis, which is to be analyzed for phase and composition of a predetermined analysis point containing an insulating material by projecting an incident electron beam on the analysis point and using scattered electrons, a conductive material is coated on a predetermined portion excluding the transmission surface through which the electrons permeate, in order to form a ground path.

The conductive material is coated onto the sample including the grid to which the sample is adhered for the analysis, and the conductive material may be gold or platinum.

It is to be understood that both the foregoing general description and the following detailed description are exemplary and explanatory and are intended to provide further explanation of the invention as claimed.

BRIEF DESCRIPTION OF THE ATTACHED DRAWINGS

The accompanying drawings, which are included to provide a further understanding of the invention and are incorporated in and constitute a part of this specification, illustrate embodiments of the invention, in which.

DETAILED DESCRIPTION OF THE PREFERRED EMBODIMENT

Reference will now be made in detail to the preferred embodiments of the present invention, examples of which are illustrated in the accompanying drawings.

Figure 1:
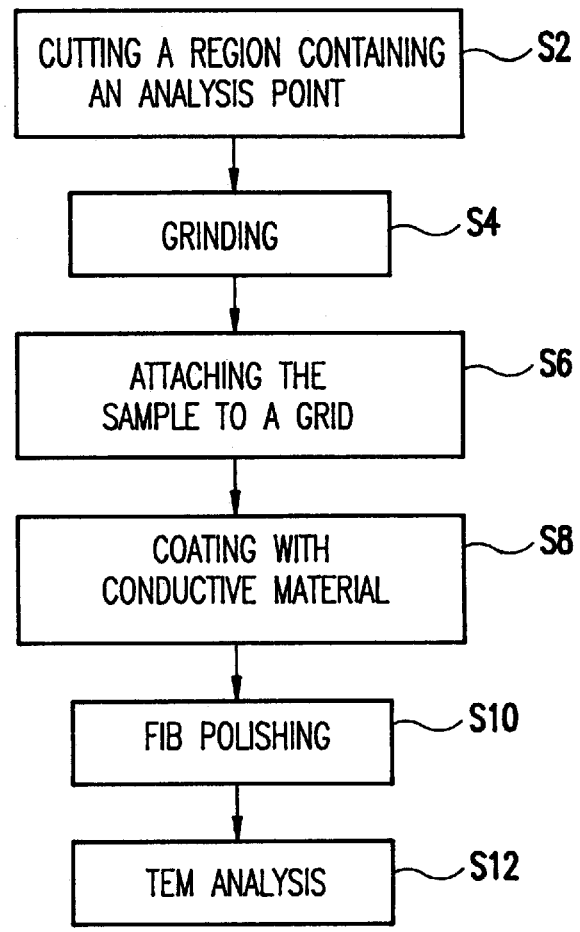
FIG. 1 is a flow chart of the process for manufacturing the sample of the present invention.

As illustrated in FIG. 1, the analysis sample of the present invention is manufactured in the following sequence: (1) cutting a region containing an analysis point from a substrate (S2); (2) grinding using the polishing process (S4); (3) attaching the sample to a grid (S6); coating the sample with gold by sputtering (S8); and FIB polishing (S10). Thereafter, the TEM analysis of the sample is performed in step (S12).

Described below is an example of manufacturing a sample by the above-mentioned procedures, in particular, a method for manufacturing a sample for analyzing the damaged pixel part of an LCD made of glass, a base layer of which is made of an insulating material.

Figure 2:
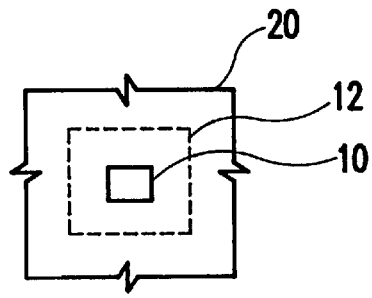
FIG. 2 is a top view of the sample of the present invention, including the analysis area, prior to the sample being cut from a substrate.
Figure 4:
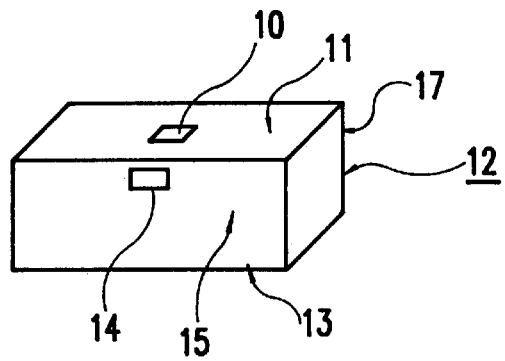
FIG. 4 is a perspective view of the sample as shown in FIG. 3, after polishing.

As illustrated in FIG. 2, an ultrasonic cutter is used to cut out a sample portion 12 of an LCD substrate 20, including analysis point 10, in which pixel loss of the LCD substrate 20 has occurred. The substrate is cut to a size of 2 mm×3 mm forming the sample 12 (step S2 in FIG. 1). As shown in FIG. 4, the sample 12 has a top 11, a bottom 13 and two sides 15 and 17.

Figure 3:
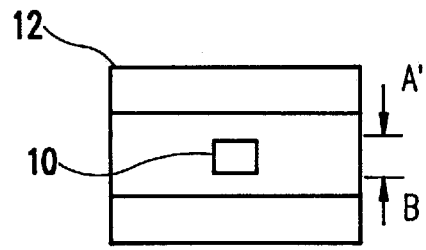
FIG. 3 is a top view of the sample of the present invention, as shown in FIG. 2, after being cut from the substrate.

In step S4, the sample 12 is polished on top 11 to a thickness of about 40 $\mu$m, measured from top 11 to bottom 13, and ground using a side to side motion in the two directions A and B as shown by the arrows in FIG. 3. The sample 12 is then polished on sides 15 and 17, as shown in FIG. 4, such that the lateral surface 14 of the analysis point 10 is exposed.

Figure 5:
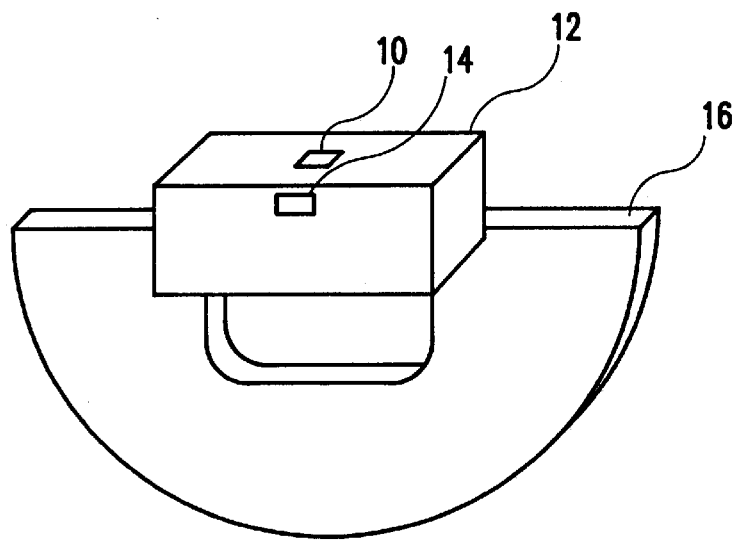
FIG. 5 is a perspective view of the sample as shown in FIG. 4, adhered to the grid.

The sample 12 ground to the configuration shown in FIG. 4, is formed such that the side 17 can be adhered to the grid 16 (see FIG. 5) with conductive adhesives to enable the analysis point 10 to face upward (step S6).

Thus adhered, a conductive material is deposited onto the top 11 and sides 15 and 17 of the sample, and also may be deposited on the grid 16 (step S8). Here, gold is used for the conductive material because of its good conductivity. Platinum may also be used as the conductive material. The conductive material is deposited by a sputtering process. The sputtering is performed for 10 minutes at the vacuum state of $10^{-2}$ Torr. A gold layer of 100 Å is deposited on the sample 12 and the grid 16 by the sputtering.

Figure 6:
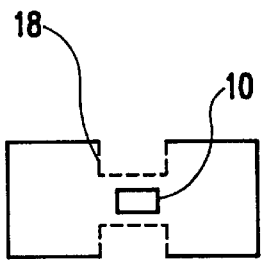
FIG. 6 is a top view of the sample as shown in FIG. 4, showing areas to be subjected to FIB etching.
Figure 7:
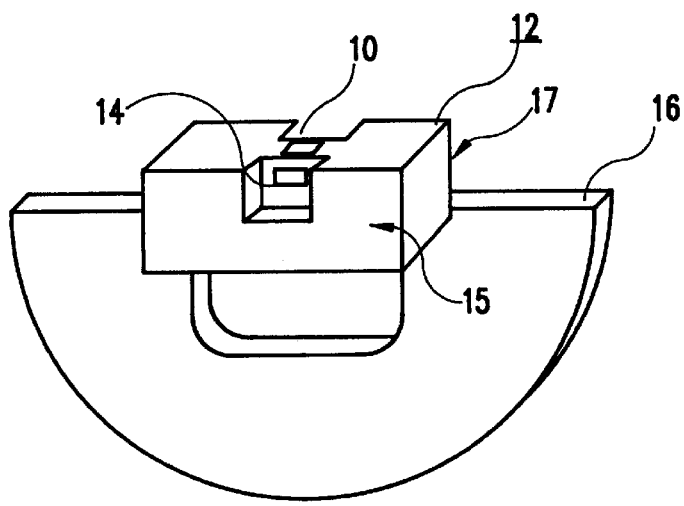
FIG. 7 is a perspective view of the sample as shown in FIG. 4, after FIB etching, and with the sample adhered to the grid.

In step S10, top 11 and sides 15 and 17 of the sample 12 on which gold is deposited are FIB-polished to a thickness of about 1000 Å, including the analysis point 10. Predetermined portions 18 of sides 15 and 17, including the lateral surface 14 on side 15, and the corresponding area of the opposite side 17 of the sample 12 as shown in FIG. 6, are fine etched as shown in FIG. 7, by the FIB polishing. This fine etching removes the conductive material from the analysis point 10 and lateral surface 14.

Figure 8:
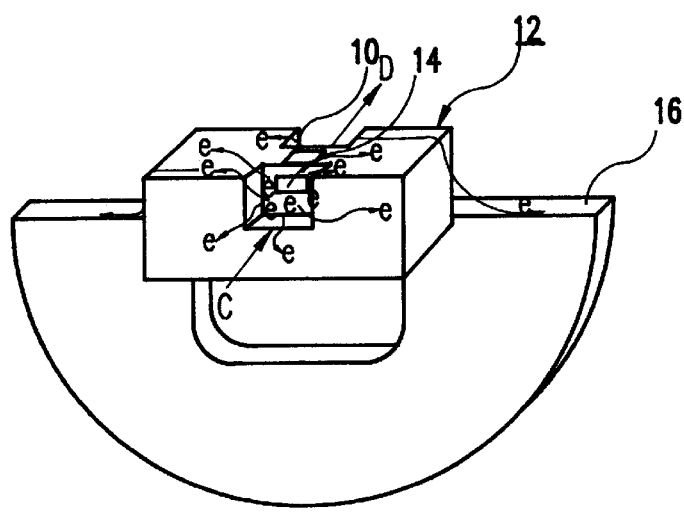
FIG. 8 shows electrons discharging from the sample as shown in FIG. 7.

Referring to FIG. 8, TEM analysis of sample 12 (step S12) will be described below, including an explanation of how the conductive (i.e, gold or platinum) layer of the present invention, which is present on the sample and the grid except in the areas of the analysis point 10 and lateral surface 14, performs a grounding function during the analysis.

During a TEM analysis, electrons are projected from the direction C to the grid 16 and sample 12. The electrons permeate lateral surface 14 of the sample 12 and are scattered in a direction D. That is, the portions 18 etched by the FIB polishing form a TEM electron projection and transmission path. Here, because an insulating layer is included in the LCD substrate sample, the transmitted electrons are caught and form charges. However, no charge remains in the insulating layer since it is discharged to the ground through the deposited conductive gold layer, which gold layer is formed in all areas except the TEM projection and transmission path. In the FIB polishing process for manufacturing the sample, no charges are formed by the ion beam focused on the sample, because the charges are discharged through the gold layers of the sample and the grid's surface.

Therefore, during FIB polishing for manufacturing the sample, and during TEM analysis, the sample having an insulating layer is not charged by capturing the electrons, since the electrons are discharged through the gold which forms the ground path. As a result, fine etching may be performed by FIB polishing, thereby preventing over-etching or under-etching.

Furthermore, during TEM analysis, electrons are transmitted through the lateral surface 14 of the analysis point. As a result, the structure of the analysis point is obtained in the form of an image created by the transmitted and scattered electrons. As the gold is deposited before FIB polishing, there is no gold in the polished portion. The image of the structure of the analysis point thus obtained using the sample of the present invention is that of the pure sample 12, and does not include the image of the gold layer.

Figure 10:
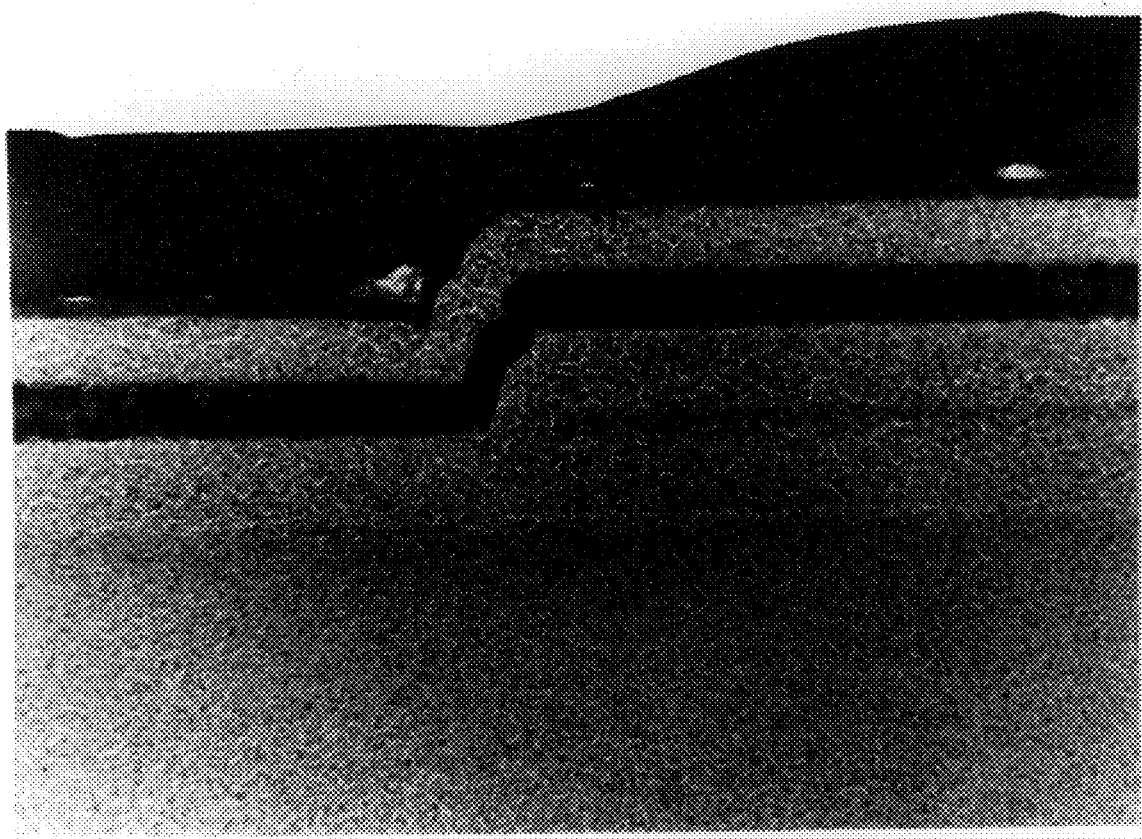
FIG. 10 is a photograph showing the TEM analysis result of a sample manufactured with gold deposition after FIB etching.
Figure 11:
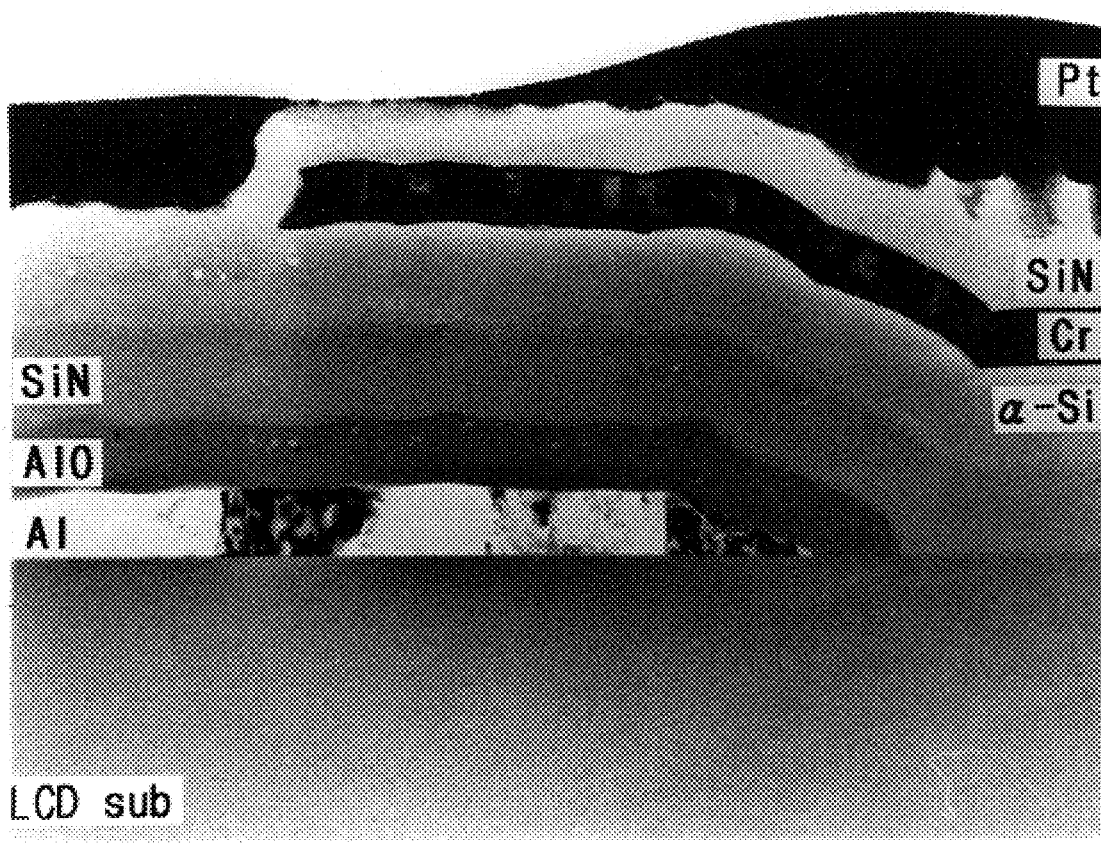
FIG. 11 is a photograph showing the TEM analysis result of the sample, such as that of FIG. 8, manufactured with gold deposition before FIB etching.

The above-mentioned result will be described in detail with reference to FIGS. 9 through 11 and Table 1.

Figure 9:
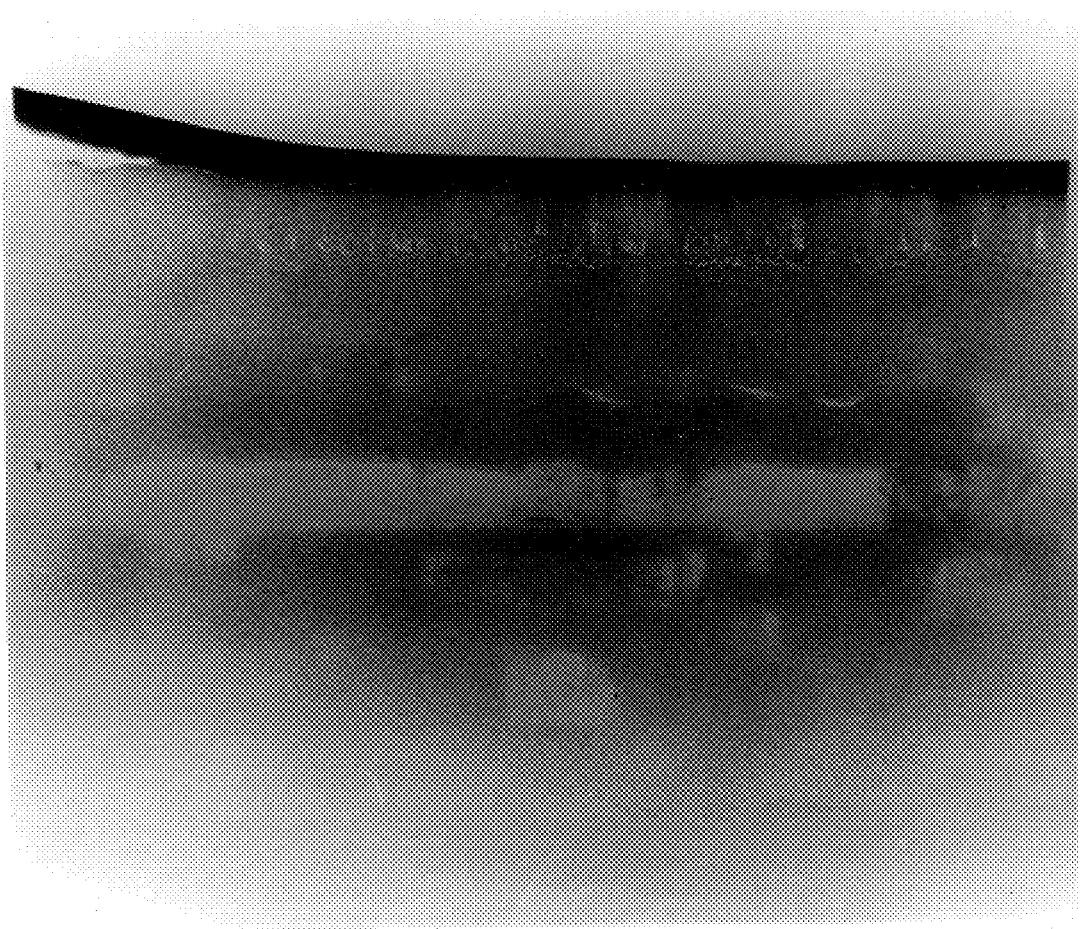
FIG. 9 is a photograph showing the TEM analysis result of a sample manufactured without gold deposition.

FIG. 9 is a TEM analysis result image, using the conventional sample in which gold is not deposited. FIG. 10 is another TEM analysis result image, using a sample manufactured by depositing gold after FIB polishing in order to prevent charge generation. FIG. 11 is still another TEM analysis result image, using the sample manufactured according to the present invention. TEM analysis results for each sample are shown in Table 1.

TABLE 1

Sample TEM Analysis Results

| evaluating →<br>manufacturing<br>method ↓ | FIB<br>polishing | TEM<br>analysis | TEM<br>image | Analysis<br>(possible/<br>impossible) |
|---|---|---|---|---|
| no gold coating | charge<br>formed | charge<br>formed | image<br>Shifted | analysis<br>impossible |
| gold coating<br>after FIB | charge<br>formed | charge<br>removed | analysis<br>point pattern<br>+ gold image | analysis<br>impossible |
| gold coating<br>before FIB | charge<br>removed | charge<br>removed | no image<br>shift + gold<br>image<br>removed | analysis<br>possible |

For the sample including an insulating body using the TEM analysis method for a conventional general conductive sample ("no gold coating"), the result is that both the FIB polishing process and TEM analysis have formed charges. In the TEM analysis of that sample, the image is shifted and blurred images are formed as illustrated in FIG. 9. Therefore, it is impossible to TEM-analyze the sample.

For the sample on which gold is deposited after FIB polishing by a method used for preventing the charges in TEM ("gold coating after FOB"), the result is the charges are removed due to the deposited gold layer during the TEM analysis, but not during the FIB polishing. The corresponding TEM analysis, as illustrated in FIG. 10, shows a blurred image resulting from the double images of the analysis point pattern and gold image. Therefore, it is impossible to TEM-analyze the sample.

On the other hand, for the sample of the present invention ("gold coating before FIB"), the results indicate that no charges are formed by either TEM analysis or FIB polishing. The images resulting from the TEM analysis are clear as illustrated in FIG. 11, and the structure of the sample can be efficiently analyzed.

In the same manner, it is also possible to TEM-analyze the causes of the defects occurring in the semiconductor's ITO layer and channel part including the insulating layer of the LCD, thereby enhancing the productivity in the production of semiconductors. In addition, as charges are not formed in FIB polishing, a usable sample for TEM analysis can be easily manufactured.

It will be apparent to those skilled in the art that various modifications and variations can be made in the sample for TEM analysis and its manufacturing method of the present invention without departing from the spirit or scope of the invention. Thus, it is intended that the present invention cover the modifications and variations of this invention provided they come within the scope of the appended claims and their equivalents.

What is claimed is:

1. A method of manufacturing a sample for transmission electron microscope analysis, comprising the steps of:

cutting from a substrate a sample of predetermined size and containing an analysis point;

grinding the sample;

adhering the sample to a grid;

forming a conductive material on a surface of the sample; and grinding the sample to a thickness such that the conductive material is removed from an area which contains the analysis point and such that charges from a focused ion beam sufficiently permeate the sample, forming an electron projection and transmission path through the sample.

2. The method as defined in claim 1, wherein said sample is an insulating material.

3. The method as defined in claim 1, wherein said sample contains an insulating material.

4. The method as defined in claim 1, wherein said sample is a part of an LCD.

5. The method as defined in claim 1, wherein said conductive material is formed both on said sample and on said grid.

6. The method as defined in claim 1, wherein said conductive material is coated on said sample.

7. The method as defined in claim 1, wherein said conductive material is coated on an entire surface of said sample.

8. The method as defined in claim 1, wherein said conductive material is deposited by means of a sputtering deposition.

9. The method as defined in claim 1, wherein said conductive material is gold.

10. The method as defined in claim 1, wherein said conductive material is platinum.

11. The method as defined in claim 1, wherein said conductive material is formed to be greater than 50 Å in thickness.

12. A sample for transmission electron microscope analysis containing insulating material, which is designed for analysis of phase and composition of a predetermined analytical point by using electrons permeating the analytical point, and then scattering, wherein a conductive material is coated on a predetermined portion of the sample other than a portion where an electron beam permeates, such that the conductive material forms a ground path for the electrons, the predetermined portion including a top surface of the sample and at least one side surface of the sample.

13. The sample as defined in claim 12, wherein said conductive material is coated on a portion including a grid adhered to said sample.

14. The sample as defined in claim 12, wherein said conductive material is gold.

15. The sample as defined in claim 12, wherein said conductive material is platinum.

16. The sample as defined in claim 12, wherein the conductive material coats all of the top surface of the sample and all of the at least one side surface of the sample other than the portion where an electron beam permeates.

17. The sample as defined in claim 12, wherein the predetermined portion includes both side surfaces of the sample.

18. The sample as defined in claim 17, wherein the conductive material coats all of the top surface of the sample and all of both side surfaces of the sample other than the portion where an electron beam permeates.

* * * * *